US00PP32190P3

(12) United States Plant Patent
Werner et al.

(10) Patent No.: US PP32,190 P3
(45) Date of Patent: Sep. 15, 2020

(54) ***PRUNUS* PLANT NAMED 'NCPR-7'**

(50) Latin Name: *Prunus cerasifera*
Varietal Denomination: NCPR-7

(71) Applicant: North Carolina State University, Raleigh, NC (US)

(72) Inventors: Dennis James Werner, Raleigh, NC (US); Layne Karlton Snelling, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/350,710

(22) Filed: Dec. 27, 2018

(65) Prior Publication Data

US 2020/0214187 P1 Jul. 2, 2020

(51) Int. Cl.
*A01H 5/08* (2018.01)
*A01H 6/74* (2018.01)

(52) U.S. Cl.
USPC ..... Plt./184
CPC ..... *A01H 6/7427* (2018.05)

(58) Field of Classification Search
USPC ..... Plt./184
CPC ..... A01H 5/00; A01H 5/02; A01H 5/0862
See application file for complete search history.

(56) References Cited

PUBLICATIONS https://issuu.com/starrosesandplants/docs/2019_star_roses_and_plants_catalog/199; Apr. 15, 2018; 3 pages.*

* cited by examiner

*Primary Examiner* — Kent L Bell
(74) *Attorney, Agent, or Firm* — Panitch Schwarze Belisario & Nadel LLP

(57) ABSTRACT

A new and distinct variety of *Prunus cerasifera Prunus* plant, herein referred to by its cultivar name, 'NCPR-7', is provided which forms dark purple colored foliage. The new variety forms moderately vigorous vegetation and provides growth habit that is weeping. The new variety is well suited for providing attractive ornamentation in the landscape.

3 Drawing Sheets

Figure 1:
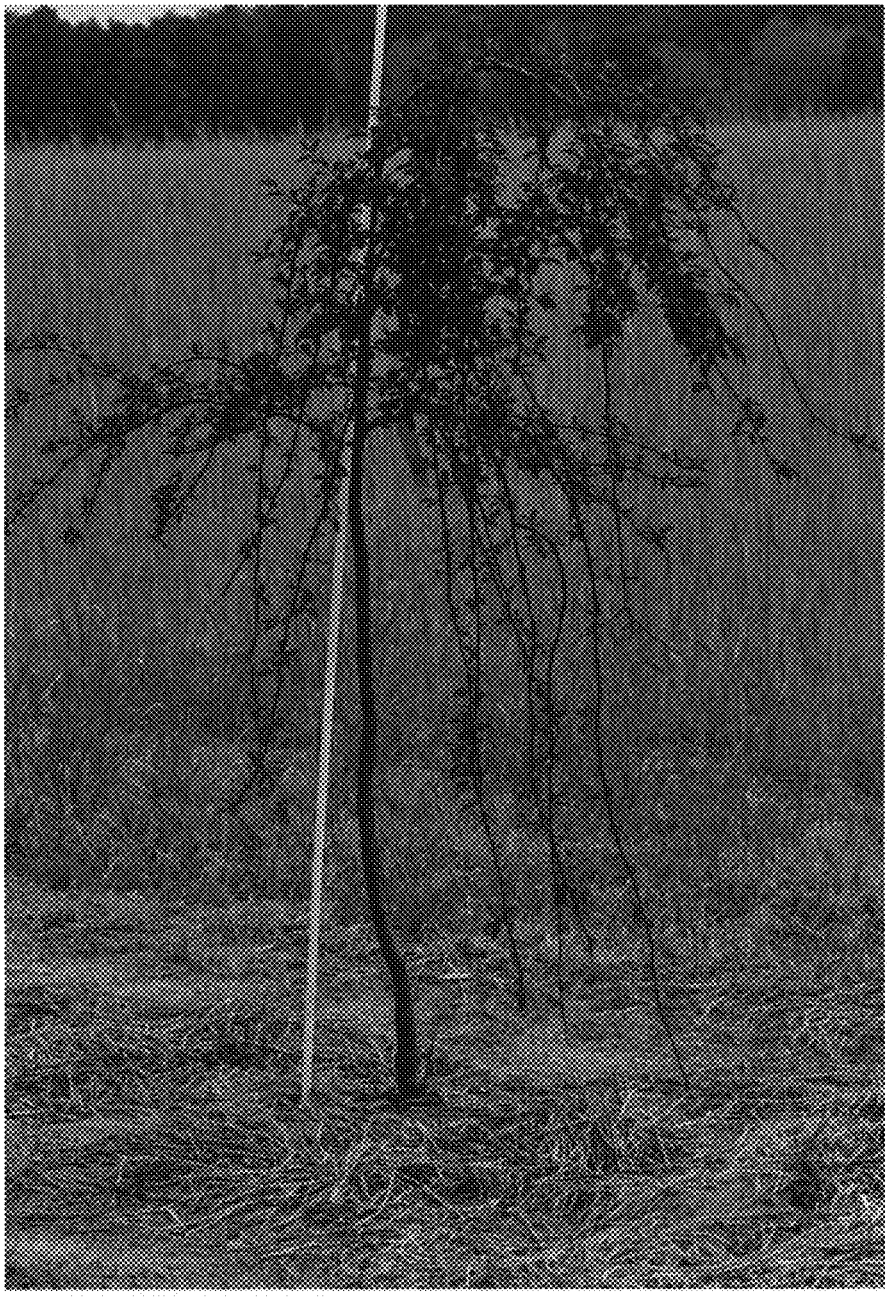

Botanical/commercial classification:
Latin name—*Prunus cerasifera.*
Common name—cherry plum.
Varietal denomination: 'NCPR-7'.

SUMMARY OF THE INVENTION

The new variety of *Prunus cerasifera* cherry plum plant was created in a controlled breeding program in 2008 at Raleigh, N.C., U.S.A., by a controlled cross wherein two parents were crossed which previously had been studied in the hope that they would contribute the desired characteristics. The female parent (i.e., the seed parent) was the 'Pendula' variety (non-patented). The male parent (i.e., the pollen parent) was the 'Atropurpurea' variety (non-patented).

The parentage of the new variety can be summarized as follows:

'Pendula' x 'Atropurpurea'

The new cultivar was discovered and selected as a single seedling within the second generation progeny of the above-stated controlled breeding program at Jackson Springs, N.C. Selective study resulted in the identification of a single plant of the new variety in 2014.

It was found that the new variety of *Prunus* plant of the present invention possesses the following combination of characteristics:

(a) forms attractive, dark purple colored foliage,
(b) exhibits weeping growth habit, and
(c) provides moderately vigorous vegetation.

The new variety well meets the needs of the horticultural industry. It can be grown to advantage as ornamentation in parks, gardens, public areas, and in residential settings. Accordingly, the plant is particularly well suited for growing in the landscape. Fruit production has not yet been observed on the new variety.

The new variety of the present invention can readily be distinguished from its ancestors. More specifically, the 'Pendula' variety (i.e., the seed parent) displays medium to dark green colored foliage and the 'Atropurpurea' variety (i.e., the pollen parent) displays light to medium-purple colored foliage and non-weeping growth habit, whereas the new variety displays dark purple colored foliage and weeping growth habit. The new variety can be distinguished from the most similar non-parental variety, *Prunus cerasifera* 'Newport' in that the comparison variety displays an upright, rounded to pyramidal habit in contrast to the weeping habit of the new variety.

The new variety has been found to undergo asexual propagation at Belvidere, Tenn. by chip budding since 2014. Asexual propagation by chip budding in Belvidere, Tenn. has shown that the characteristics of the new variety are stable and are strictly transmissible by such asexual propagation from one generation to another. Accordingly, the new variety undergoes asexual propagation in a true-to-type manner.

The new variety has been named 'NCPR-7'.

BRIEF DESCRIPTION OF THE PHOTOGRAPHS

The accompanying photographs shows as nearly true as it is reasonably possible to make the same, in color illustrations of this character, typical specimens of the new variety. Colors in the photographs may differ slightly from the color values cited in the detailed description, which accurately describes the colors of the new variety. The *Prunus* plants of the new variety were approximately two years of age and were observed at the beginning of the third growing season during March and April of 2017 at Jackson Spring, N.C., U.S.A. while growing outdoors.

FIG. 1—illustrates a specimen the tree—side view.

Figure 2:
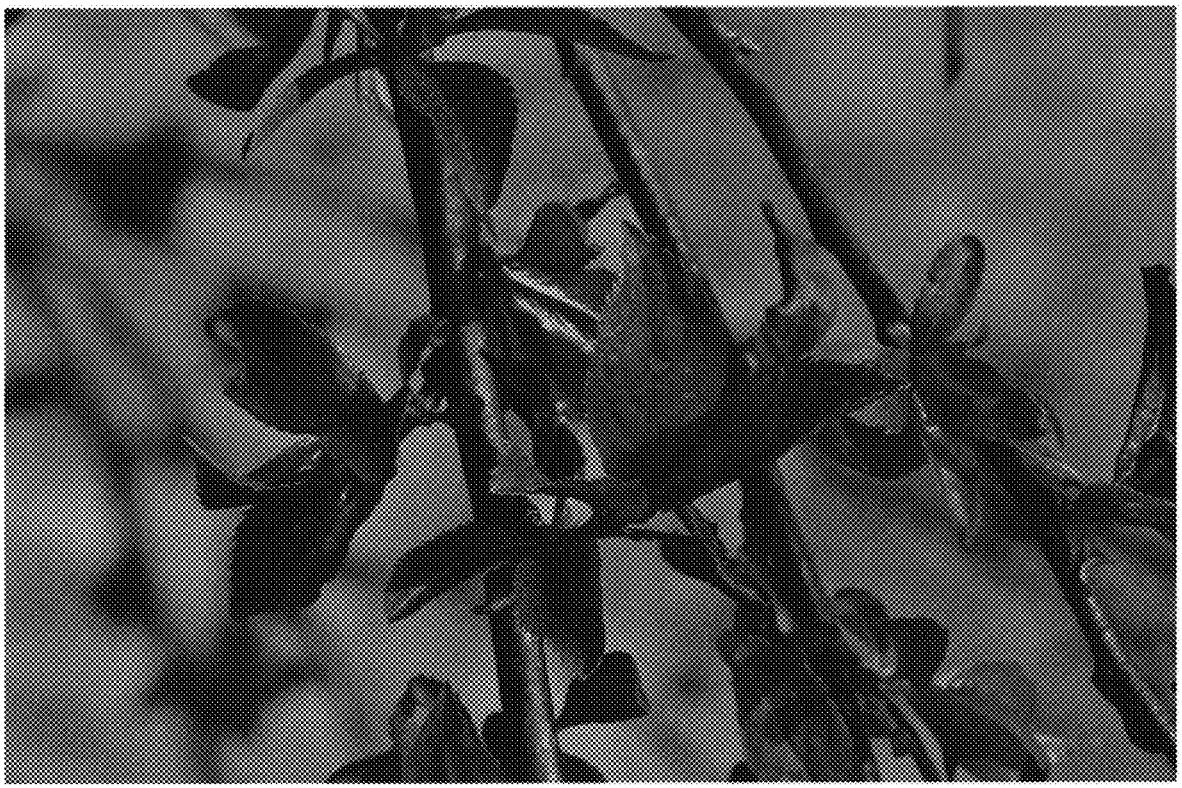

FIG. 2—illustrates a specimen of the emerging foliage.

Figure 3:
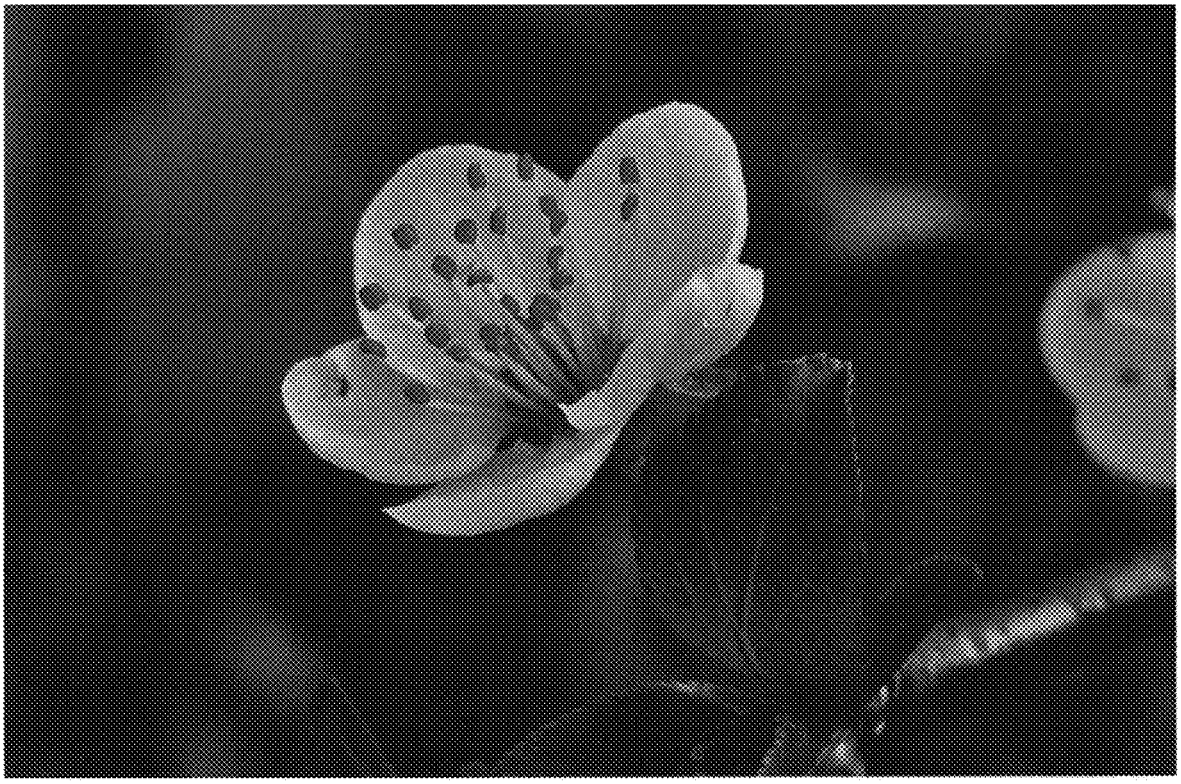

FIG. 3—illustrates a specimen of a flower.

DETAILED BOTANICAL DESCRIPTION

The chart used in the identification of the colors is that of The Royal Horticultural Society (R.H.S. Colour Chart, 2007 edition), London, England. The terminology which precedes reference to the chart has been added to indicate the corresponding color in more common terms. The description is based on the observation of approximately three-years-old specimens of the new variety during February and March 2018 under natural light conditions at Jackson Springs, N.C., U.S.A. produced from chip budding and growing outside. Measurements and numerical values represent averages of typical plants.

Class: *Prunus* Plant.

Plant:

*Habit*.—Weeping.

*Type*.—Deciduous perennial tree.

*Height*.—Approximately 2.13 meters on average.

*Width*.—Approximately 1.3 meters on average.

*Trunk*.—Diameter immediately above graft union: approximately 4.8 cm on average. — texture: slightly rugose.

Branches:

*Habit*.—Highly branched.

*Strength*.—Moderately strong.

*Color*.—Young stems: commonly near Purple Group N77A. — mature stems: commonly near Greyed-Purple Group N187B.

*Diameter*.—New growth: approximately 2.0 mm on average. — one-year old growth: approximately 3.4 mm on average.

*Lenticel*.—General: numerous, tiny. — length: commonly less than 1.0 mm. — shape: elliptic. — color: commonly near Brown Group N200B.

*Texture*.—New growth: glabrous.

Foliage:

*Type*.—Deciduous.

*Arrangement*.—Alternate.

*Leaves*.—Length: approximately 5.6 cm on average. — width: approximately 3.2 cm on average. — shape: elliptic; apex is acute; base is rounded to cuneate. — margin: serrate. — venation pattern: pinnate. — texture of upper and lower surfaces: smooth, glabrous. — color of upper and lower surfaces of mature foliage: commonly near Purple Group N77A. — fragrance: none detected.

*Petiole*.—Length: approximately 1.2 cm on average. — diameter: approximately 1.1 mm on average. — texture: smooth, glabrous. — color: commonly near Purple Group N77A.

Flowering description:

*General description*.—Compound corymbs. — aspect: facing upward to slightly outward. — quantity per plant: numerous. — fragrance: slightly sweet. — flower diameter: approximately 1.5 cm on average. — flower height: approximately 1.4 cm on average.

*Pedicel*.—Strength: strong. — shape: rounded. — aspect: erect to about 45° from branch axis. — length: approximately 0.8 cm on average. — diameter: approximately less than 1.0 mm on average. — texture: glabrous. — color: commonly near Red-Purple Group 59C.

Flower description:

*General description*.—Type: single, rotate, not persistent. — aspect: upright. — quantity per inflorescence: approximately 1 flower per flower bud.

*Bud just before opening*.—Shape: ovate tapering to a point. — length: approximately 2.4 cm on average. — diameter: approximately 1.0 mm on average. — color: commonly near Red-Purple Group 59A. — texture: glabrous.

*Petals*.—Quantity per flower: approximately 5, unfused. — shape: orbicular; apex is rounded; base is obtuse. — margin: entire. — length: approximately 9.0 mm on average. — width: approximately 8.0 mm on average. — texture of upper and lower surfaces: glabrous. — color of upper and lower surfaces when first and fully open: commonly near Red-Purple Group 73D.

*Calyx*.—Shape: vase-shaped; 5 rounded lobes at terminus. — length: approximately 4.8 mm on average. — diameter: approximately 3.0 mm at top of hypanthium on average. — color of outer and inner surfaces: commonly near Red-Purple Group 72B. — texture of inner and outer surfaces: glabrous.

*Sepals*.—Quantity: commonly 5, attached to top of hypanthium. — arrangement: in a single whorl.

*Pedicel*.—Strength: strong. — shape: round. — length: approximately 0.8 cm on average. — diameter less than 1.0 mm on average. — texture: glabrous. — color: commonly near Red-Purple Group 59C.

*Stamen*.—Quantity: approximately 21 on average per flower, unfused and attached to apex of hypanthium. — length: approximately 3.0 mm on average.

*Filament*.—Length: approximately 5.0 mm on average. — color: commonly near Red-Purple Group 65C.

*Anther*.—Shape: round to slightly oblong. — length: commonly less than 1.0 mm. — width: commonly less than 1.0 mm. — color: commonly near Red-Purple Group 65C.

*Pollen*.—Amount is sparse and color is commonly near Yellow Group 9C.

*Pistil*.—Quantity: commonly 1 per flower. — length: approximately 1.0 mm on average. — width: commonly less than 1.0 mm. — color: commonly near Red-Purple Group 59B. — texture: glabrous.

*Stigma*.—Shape: round. — color: commonly near Red-Purple Group 72A. — length: commonly less than 1.0 mm. — width: commonly less than 1.0 mm.

*Style*.—Shape: elongate. — width: commonly less than 1.0 mm. — color: commonly near Red-Purple Group 72A.

*Ovary*.—Position: superior. — shape: round. — width: commonly less than 1.0 mm on average. — color: commonly near Red-Purple Group 72A.

*Seeds*.—None observed.

Development:

*Growth time*.—Approximately 1.5 years from budding to finish as a 4 to 6 foot tree.

*Vegetation*.—Moderately vigorous.

*Flowering season*.—Flowers in late winter to early spring.

*Resistance to disease*.—Resistance to pathogens and pests common to *Prunus* plants has not been observed.

The new 'NCPR-7' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of *Prunus* plant characterized by the following combination of characteristics:

(a) forms attractive, dark purple colored foliage, (b) exhibits weeping growth habit, and (c) provides moderately vigorous vegetation;

substantially as herein shown and described.

* * * * *